United States Patent
Monroe et al.

[11] Patent Number: 6,113,608
[45] Date of Patent: Sep. 5, 2000

[54] STENT DELIVERY DEVICE

[75] Inventors: Lance A. Monroe, New Hope; Andrew D. Bicek, Big Lake; Anthony C. Vrba, Maple Grove, all of Minn.

[73] Assignee: Scimed Life Systems, Inc., Maple Grove, Minn.

[21] Appl. No.: 09/196,793

[22] Filed: Nov. 20, 1998

[51] Int. Cl.⁷ .......................... A61M 29/00; A61M 5/00
[52] U.S. Cl. ............................. 606/108; 604/264
[58] Field of Search .................... 606/108, 198; 604/264, 96

[56] References Cited

U.S. PATENT DOCUMENTS

| | | | |
|---|---|---|---|
| 3,911,927 | 10/1975 | Rich et al. | 128/349 |
| 4,328,811 | 5/1982 | Fogarty | 128/774 |
| 4,572,186 | 2/1986 | Gould et al. | 128/341 |
| 4,606,347 | 8/1986 | Fogarty et al. | 128/344 |
| 4,649,922 | 3/1987 | Wiktor | 128/344 |
| 4,655,771 | 4/1987 | Wallsten | 623/1 |
| 4,665,918 | 5/1987 | Garza et al. | 128/343 |
| 4,681,110 | 7/1987 | Wiktor | 128/343 |
| 4,699,611 | 10/1987 | Bowden | 604/51 |
| 4,732,152 | 3/1988 | Wallstén et al. | 128/343 |
| 4,848,343 | 7/1989 | Wallstén et al. | 128/343 |
| 4,863,440 | 9/1989 | Chin | 604/271 |
| 4,875,480 | 10/1989 | Imbert | 128/343 |
| 4,893,623 | 1/1990 | Rosenbluth | 606/192 |
| 4,950,227 | 8/1990 | Savin et al. | 604/8 |
| 4,954,126 | 9/1990 | Wallstén | 600/36 |
| 4,990,138 | 2/1991 | Bacich et al. | 604/96 |
| 5,026,377 | 6/1991 | Burton et al. | 606/108 |
| 5,061,275 | 10/1991 | Wallstén et al. | 623/1 |
| 5,064,435 | 11/1991 | Porter | 623/12 |
| 5,071,407 | 12/1991 | Termin et al. | 604/104 |
| 5,074,845 | 12/1991 | Miraki et al. | 604/101 |
| 5,078,720 | 1/1992 | Burton et al. | 606/108 |
| 5,108,416 | 4/1992 | Ryan et al. | 606/194 |
| 5,158,548 | 10/1992 | Lau et al. | 604/96 |
| 5,192,297 | 3/1993 | Hull | 606/195 |
| 5,201,757 | 4/1993 | Heyn et al. | 606/198 |
| 5,234,457 | 8/1993 | Anderson et al. | 606/198 |
| 5,242,399 | 9/1993 | Lau et al. | 604/104 |
| 5,261,878 | 11/1993 | Galindo | 604/96 |
| 5,381,661 | 1/1995 | Malina | 60/560 |
| 5,445,646 | 8/1995 | Euteneuer et al. | 606/198 |
| 5,507,768 | 4/1996 | Lau et al. | 606/108 |
| 5,534,007 | 7/1996 | St. Germain et al. | 606/108 |
| 5,571,135 | 11/1996 | Fraser et al. | 606/198 |
| 5,571,168 | 11/1996 | Toro | 623/1 |
| 5,626,603 | 5/1997 | Venturelli et al. | 606/198 |
| 5,690,643 | 11/1997 | Wijay | 606/108 |
| 5,690,644 | 11/1997 | Yurek et al. | 606/108 |
| 5,695,468 | 12/1997 | Lafontaine et al. | 604/96 |
| 5,702,418 | 12/1997 | Ravenscroft | 606/198 |
| 5,707,376 | 1/1998 | Kavteladze et al. | 606/108 |
| 5,709,703 | 1/1998 | Lukic et al. | 606/198 |
| 5,733,267 | 3/1998 | Del Toro | 604/280 |
| 5,766,192 | 6/1998 | Zacca | 606/159 |
| 5,772,669 | 6/1998 | Vrba | 606/108 |
| 5,810,871 | 9/1998 | Tuckey et al. | 606/198 |
| 5,817,101 | 10/1998 | Fiedler | 606/108 |
| 5,928,258 | 7/1999 | Khan et al. | 606/191 |
| 5,944,726 | 8/1999 | Blaeser et al. | 606/108 |
| B1 4,733,665 | 1/1994 | Palmaz | 606/108 |

FOREIGN PATENT DOCUMENTS

95/11055  4/1995  WIPO.

*Primary Examiner*—Paul J. Hirsch
*Assistant Examiner*—Michael B. Priddy
*Attorney, Agent, or Firm*—Vidas, Arrett & Steinkraus

[57] ABSTRACT

A stent delivery system having a hydraulically actuated retractable sheath is disclosed. A pressurizing fluid is either supplied by an inflation lumen to a portion of a piston housing or is withdrawn from a portion of a piston housing, thereby actuating a piston. As the piston moves, a retractable sheath which is connected to the piston moves as well causing the sheath to retract.

41 Claims, 4 Drawing Sheets

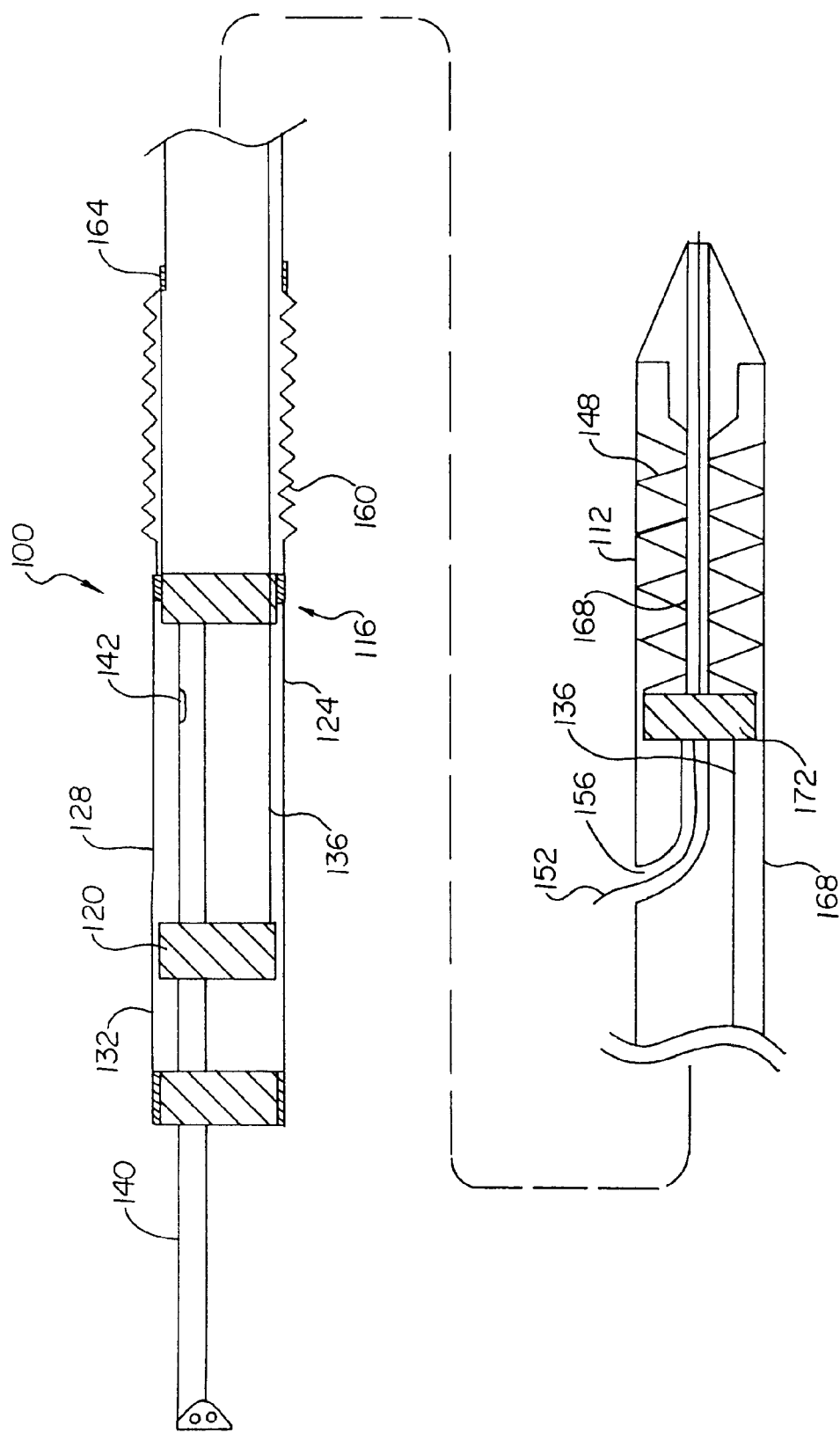

STENT DELIVERY DEVICE

BACKGROUND OF THE INVENTION

Stent delivery systems for deploying stents are a highly developed and well known field of medical technology. Stents have many well known uses and applications. A stent is a prosthesis which is generally tubular and which is expanded radially in a vessel or lumen to maintain its patency. Stents are widely used in body vessels, body canals, ducts or other body lumens.

The delivery systems for stents are generally comprised of catheters with the stent axially surrounding the distal end of the catheter. It is highly desirable to keep the profile of the catheter as small as possible. Therefore, self-expanding stents are generally confined in a reduced radius for delivery to the deployment site. Once the stent is deployed the catheter is removed, leaving the stent implanted at the desired location to keep the vessel walls from closing.

A variety of techniques have been developed for holding a self-expanding stent in its reduced configuration while moving the distal end of the catheter to the deployment site. For example, in U.S. Pat. No. 4,655,771 to Wallsten, gripping members at either end of the stent hold the stent in an axially-elongated position, which causes the stent to take a reduced radius delivery configuration.

Another common technique for maintaining the self-expanding stent in a reduced radius delivery configuration is using a sheath which surrounds the stent and compresses it around the catheter. This technique is disclosed in U.S. Pat. No. 5,071,407 to Termin and U.S. Pat. No. 5,064,435 to Porter, both of which use a silicon rubber sheath to compress the stent. A similar technique is disclosed in U.S. Pat. No. 5,026,377 to Burton and U.S. Pat. No 5,078,720 to Burton.

Unfortunately, deployment of stents, in particular, long and/or large stents, which are held in place by sheaths applying high frictional forces and compressive forces, can be quite difficult. Use of a manually operated pull-wire is not always adequate to retract a sheath. It is therefore desirable to provide a means for retracting sheaths which can apply sufficient force to overcome these high forces.

To that end, a catheter employing a piston-based hydraulic sheath retraction mechanism has been disclosed in co-pending, commonly assigned U.S. patent application Ser. No. 08/633,726, the entire contents of which are incorporated herein in its entirety by reference. Further to that end, the present invention provides a medical device delivery apparatus which employs a piston-based hydraulically operated retraction mechanism to apply sufficient force to the retractable sheath so as to withdraw the sheath from its initial position over the stent. The present invention also provides methods of delivering a medical device using a medical device delivery apparatus comprising a hydraulically operated piston.

SUMMARY OF THE INVENTION

In a general way, the present invention provides a mechanism for retracting a sheath to allow delivery of a medical device to a desired bodily location. Specifically, the medical device delivery apparatus comprises an elongate flexible catheter. At the distal end of the catheter is a medical device receiving region. A retractable sheath surrounds the medical device receiving region of the elongate catheter. Attached to the retractable sheath is a retraction device for retracting the retractable sheath. The retraction device comprises a piston housing having a first portion and a second portion therein. A movable piston contained within the housing separates the first and second portions. The first portion has an inflatable element therein which is capable of applying a force to the piston so as to actuate the piston. Finally, a connecting member is connected at one end to a pull collar which is attached to the retractable sheath and at the other end to the piston.

In another embodiment, the medical device delivery apparatus is similar to that described above, however, the piston housing surrounds and is coaxial with a portion of the elongate flexible catheter. Further, the inflatable element is optional.

In yet another embodiment of the invention, the piston is characterized in that a transverse cross-section of the piston housing extends across a substantial portion of a transverse cross-section of the apparatus in the region of the piston.

In all of the above-described embodiments, the piston may pull or push the retractable sheath depending on whether the first portion of the housing is distal to the second portion of the housing or vice versa.

Moreover, in all of the above-described embodiments, the piston may be actuated by supplying an inflation fluid to the inflatable element or first housing portion. The inflation fluid for use in conjunction with the present invention is desirably biocompatible such as saline. Alternatively, the medical device delivery apparatus may be initially supplied with a fluid to the inflatable element or first housing portion and the piston then actuated by removing the fluid therefrom.

The invention is also directed to methods of delivering a medical device to a desired bodily location. Specifically, the invention entails providing any of the inventive medical device delivery apparatuses disclosed herein with a stent or other medical device surrounding the medical device receiving region. At least a portion of the apparatus is inserted in a bodily vessel and the stent or medical device advanced to a desired location. A source of fluid is provided and the fluid supplied under pressure to the inflatable element so as to actuate the piston and retract the sheath. The stent is deployed and the medical device delivery apparatus withdrawn from the bodily vessel.

The invention is also directed to methods of delivering a medical device to a desired bodily location using any of the inventive medical device delivery apparatuses disclosed herein by first supplying a fluid to the first piston housing and, after insertion of the apparatus in the bodily vessel and maneuvering the stent or medical device into position, removing at least some of the fluid from the first piston housing so as to actuate the piston and retract the sheath in order to deploy the stent.

BRIEF DESCRIPTION OF THE FIGURES

FIG. 4 is a side elevational section of a rapid exchange embodiment of the present invention showing a stent deployment device with a hydraulically actuated retraction mechanism.

DETAILED DESCRIPTION OF THE INVENTION

The following detailed description should be read with reference to the drawings in which similar parts in different drawings are numbered the same. The drawings, which are not necessarily to scale, depict exemplary embodiments and are not intended to limit the scope of the invention.

Examples of materials, dimensions, assemblies and manufacturing processes are provided for selected parts. All other parts employ that which is known to those skilled in the field of the invention. Those skilled in the art will recognize that many of the examples provided have suitable alternatives which may also be utilized.

Figure 1:
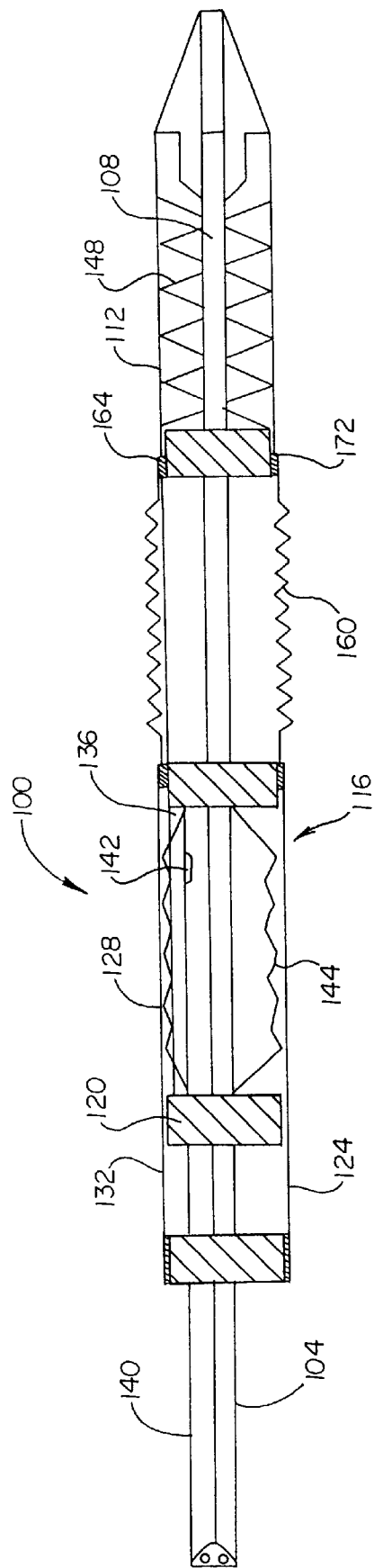
FIG. 1 is a side elevational section showing a stent deployment device with a hydraulically actuated retraction mechanism including an inflatable element.

A side elevational view of the distal end of an embodiment of the inventive medical device delivery apparatus is shown generally at 100 in FIG. 1. The device includes an elongate flexible catheter 104. At the distal end of catheter shaft 104 is a medical device receiving region 108. A retractable sheath 112 surrounds medical device mounting region 108 of catheter 104. Retractable sheath 112 is operably connected to a retraction device, shown generally at 116, for retracting retractable sheath 112. Retraction device 116 includes a moveable piston 120 within a piston housing 124, piston 120 separating first portion 128 of piston housing 124 from second portion 132 of piston housing 124. First portion 128 of housing 124 is distal to second portion 132 of piston housing 124. Piston 120 is proximal to retractable sheath 112. A connecting member 136 also extends from piston 120 to pull collar 164 which is connected to retractable sheath 112 so that movement of the piston will result in an associated movement of the retractable sheath. Piston 120 is actuated by the supply of a fluid to first portion 128 of piston housing 124. The fluid is supplied by inflation lumen 140 which extends to the proximal end of the device. Inflation lumen 140 is capable of fluid communication with the first portion of the piston housing via an opening 142 in the inflation lumen.

As shown in FIG. 1, first portion 128 of piston housing 124 further contains an inflatable element 144 within. Inflatable element 144 is capable of fluid communication with inflation lumen 140. As fluid is supplied to inflatable element 144, inflatable element 144 expands so as to contact piston 120 and ultimately move piston 120 in a proximal direction. Because of the coupling between piston 120 and retractable sheath 112, as piston 120 is displaced proximally by inflatable bladder 144, retractable sheath 112 retracts from over medical device mounting region 108 in a proximal direction to expose medical device mounting region 108 or any medical device such as stent 148 mounted thereon. As operated in this mode, the retraction device functions as a pull device in that the retractable sheath is pulled from its unretracted position.

Retractable sheath 112 may further be returned to its unretracted position by withdrawing the fluid from inflatable element 144 and applying a suitable vacuum to inflatable element 144. In this mode, retraction device 116 is acting as a push device, pushing sheath 112.

Similarly, the device can be configured to retract sheath 112 in a distal direction by first supplying a fluid to inflatable element 144 so as to inflate inflatable element 144. Retractable sheath 112 may then be retracted distally by withdrawing the fluid and pulling a vacuum on inflatable element 144. The resulting distal movement of piston 120 is coupled with distal movement of retractable sheath 112. Sheath 112 may similarly be returned to its unretracted position by supplying a fluid to inflatable element 144.

Although a tight fit between the piston and the piston housing is desirable it is not absolutely necessary in the embodiment of FIG. 1 because the inflation fluid is contained within an inflatable element. Thus, regardless of whether the first and second piston housings are isolated from one another, the inflatable element can still actuate and move the piston on inflation or deflation.

Figure 2:
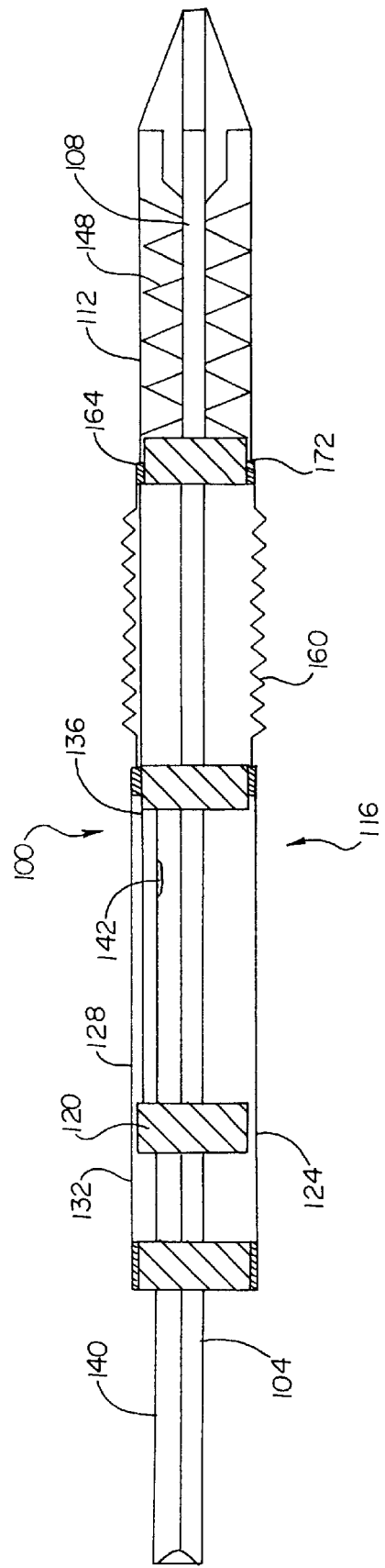
FIG. 2 is a side elevational section of another embodiment of the present invention showing a stent deployment device with a hydraulically actuated retraction mechanism without an inflatable element.

Although an inflatable element is shown in FIG. 1, its presence is optional. In the embodiment shown in FIG. 2, the device differs from that shown in FIG. 1 only in the absence of an inflatable element as shown in FIG. 1. In the device of FIG. 2, the inflation fluid is supplied directly into the interior of first portion 128 of piston housing 124 via inflation lumen 140. The fluid directly impinges on the piston and the fluid pressure actuates the piston.

Desirably, in such an embodiment, the first and second piston housings will be isolated from one another to prevent leakage of the inflation fluid from the first piston housing into the second piston housing. Such leakage would tend to equalize the pressure in the first and second piston housings, thereby preventing or reducing the ability of the piston to retract the sheath.

Leakage from one housing to the other housing may be reduced by using a piston that fits tightly in the piston housing, although not so tightly that it cannot be actuated. The piston also must form a tight fit with the catheter that runs therethrough. Alternatively, the piston may be slidably sealed to the piston housing. As such, the piston may be tethered all along its periphery to the piston housing via a thin, flexible sheet of material such as Teflon. The material should be of sufficient length to allow for desired range of motion of the piston. The piston may similarly be slidably sealed to the catheter that runs therethrough.

The use of slidably sealed components has been disclosed in co-pending commonly assigned U.S. patent application Ser. No. 08/722,834 filed Sep. 27, 1996, and a continuation-in-part application Ser. No. 09/071,484 filed May 1, 1998. The entire contents of both applications are hereby incorporated in their entirety by reference.

Use of a suitable lubricant, desirably biocompatible, on the piston, piston housing and catheter portion that traverses the piston may facilitate sliding of the piston within the housing.

As in the embodiment of FIG. 1, the device may be used in both the push mode and in the pull mode.

Figure 3:
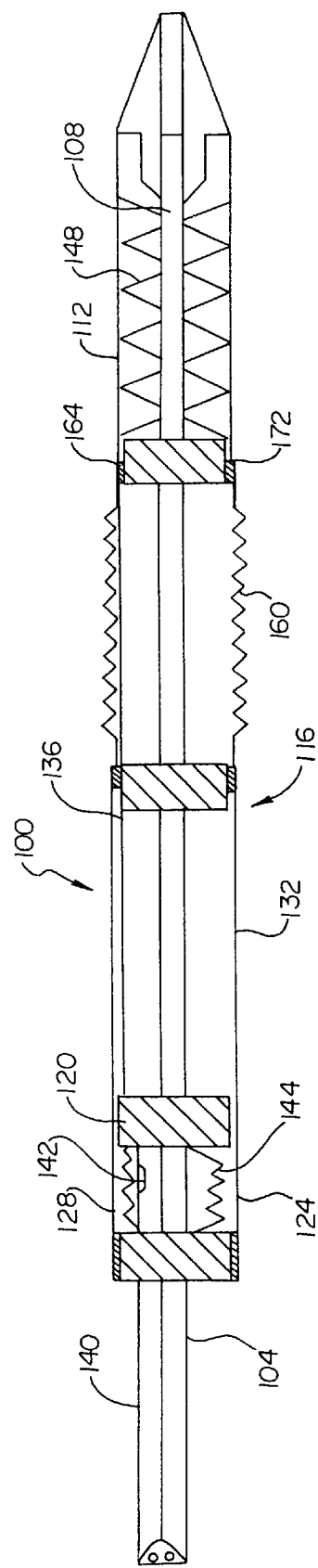
FIG. 3 is a side elevational section of another embodiment of the present invention showing a stent deployment device with a hydraulically actuated retraction mechanism.

In another embodiment of the invention, as shown in FIG. 3, first portion 128 of piston housing 124 is proximal to second portion 132 of piston housing 124. As in the previous embodiments, a fluid is supplied to first portion 128 of piston housing 124 so as to actuate piston 120. The device so operates in push mode with sheath 112 being retracted by piston 120 pushing it.

Although inflatable element 144 is shown in FIG. 3, the presence of the inflatable element is optional. Desirably, in the absence of the inflatable element, the first and second piston housing will be isolated from one another such as by slidably sealing piston 120 to piston housing 124 and to catheter shaft 104 as discussed above.

The device may also be employed with a fluid already supplied to first portion 128 of piston housing 124. Piston 120 is then actuated by withdrawing the fluid and applying a vacuum to first portion of housing 124. As such, the device operates in pull mode.

In any of the above embodiments, an additional guide wire (not shown) may extend through catheter 104 to the distal end of the device. The inventive devices may also be made in fixed wire embodiments as are known in the art. In the case of the fixed-wire design, the guidewire is fixedly attached to the medical device delivery system. A fixed-wire delivery system is described in U.S. Pat. No. 5,702,364 to Euteneuer et al., incorporated herein in its entirety by reference, and may be suitably modified for use with the inventive medical device delivery system.

Although in the previous embodiments, the piston housing surrounds and is coaxial with a portion of the elongate flexible catheter, the invention also contemplates embodiments in which the piston does not surround any portion of the catheter. As such, the invention is also directed to a medical device delivery apparatus for implantation of a medical device in a vessel which comprises an elongate flexible catheter having proximal and distal ends. The catheter has a medical device receiving region at the distal end thereof. A retractable sheath surrounds at least a portion of the medical device receiving region. Operably connected to the retractable sheath is a retraction device for retracting the retractable sheath. The retraction device comprises a piston housing having a first and a second portion therein. The first and second portions are separated by a movable piston contained within the housing. The piston housing surrounds and is coaxial with a portion of the elongate flexible catheter. Connecting the piston and the retractable sheath via the pull collar is a connecting member. Fluid is supplied to the first piston housing via an inflation lumen. An inflatable bladder capable of fluid communication with the inflation lumen may optionally be present in the first piston housing.

An example of such a device is shown in FIG. 4. The device of FIG. 4 is similar to the embodiment of FIG. 2, modified for use as rapid exchange catheter. Desirably, guidewire 152 enters the device through guidewire port 156 in distal outer tube 168 located toward the distal end of the device. Distal outer tube 168 has a longitudinal groove therein to accommodate guidewire 152 on retraction of the sheath. Of course, in other configurations, the guidewire may enter the apparatus through a guidewire port located proximal of the piston. Regardless of the location of the guidewire port, the guidewire extends proximally to the proximal end of the device and beyond.

In the rapid-exchange embodiment of FIG. 4, only a portion of the medical device delivery apparatus rides on the guidewire. Typically, the usable length of the medical device delivery system is approximately 135 cm. For a rapid-exchange medical device delivery system, the distance from where the guide wire accesses the inner tube to the distal tip will be approximately 5 cm to 45 cm. Other suitable features of a rapid exchange device may also be incorporated into the present apparatus, including those suitable features disclosed in U.S. Pat. No. 5,534,007 to St. Germain et al., incorporated herein in its entirety by reference.

Although the device as shown in FIG. 4 does not have an inflatable element, an inflatable element similar to that shown in FIG. 1 may be included in first portion 128 of housing 124. Similarly, the device of FIG. 4 may be configured similarly to that shown in FIG. 3, with the first portion of the piston housing proximal to the second portion of the housing. Again, an inflatable element is optionally present in such an embodiment.

The invention also contemplates a medical device delivery apparatus in which a transverse cross-section of the piston housing extends across a substantial portion of a transverse cross-section of the apparatus in the region of the piston. To that end, the medical device delivery apparatus comprises an elongate flexible catheter extending longitudinally and having proximal and distal ends. The catheter has a medical device receiving region at the distal end thereof. A retractable sheath surrounds at least a portion of the medical device receiving region of the elongate catheter. The retractable sheath may be retracted via a retraction device. The retraction device comprises a piston housing having a first and a second portion therein which are separated by a movable piston contained within the housing. A connecting member extends from a pull collar which is in contact or mechanical communication with the retractable sheath to the piston. The piston on actuation moves in a longitudinal direction. The apparatus is further characterized in that a transverse cross-section of the piston housing extends across a substantial portion of a transverse cross-section of the apparatus in the region of the piston. Several different embodiments incorporating this feature are shown in FIGS. 1–4.

Although the inflatable element may be formed in a variety of different shapes, it is desirably accordion shaped and designed to expand in a longitudinal direction upon inflation so as to apply a force to the piston. Desirably, the inflatable element is bonded at one end to the inner tube and at the other end to the piston. Suitable materials for the inflatable element include polyolefin copolymer, polyester, polyethylene terephthalate, polyethylene, polyether block amide, polyamide, polyimide, nylon, latex and urethane as well as other suitable balloon materials as are known in the art.

Inflation fluid may be supplied to or removed from the first portion of the piston housing via an inflation lumen. The inflation lumen may be made of suitable materials as are known in the art including polyethylenes, polyimides and polyolefin copolymers. Although only one opening is shown in the inflation lumens in the figures, the inflation lumen may have additional openings therein. The hole may be a nick in the inflation large enough for inflation fluid to flow therethrough.

The second portion of the piston housing may be sealed or have one or more openings therein. The presence of one or more openings may help prevent the build-up of pressure in the second piston housing as the piston is actuated and the volume of the second piston housing decreased. Where the second piston housing is proximal to the first piston housing, the second piston housing may also be capable of fluid communication with a manifold at the proximal end of the catheter. To avoid the possibility of air bleeding from the second piston housing into the body where there are openings in the second piston housing, the second piston housing may be primed with a biocompatible fluid.

Each embodiment of the inventive apparatuses may be operated in one of two modes. In the first mode, as disclosed above, the piston is actuated by supply of a fluid to the first portion of the piston housing. In the second mode of operation, the piston is actuated by removal of a fluid from the first piston housing. As the fluid is removed and a vacuum drawn on the first piston housing, the piston moves from its initial position retracting the sheath. Desirably in this case, the opening in the inflation lumen will be at the opposite end of the first piston housing from the piston.

In all of the above embodiments, it should be noted that where a vacuum is applied to the piston housing, the vacuum cannot be so low as to damage the device.

The second mode of operation may also be carried out by securing the piston to the piston housing by an elastic or otherwise resilient joining member. The joining member may be a spring placed behind the piston or a rubber bladder. While fluid is present in the first piston housing, the piston is displaced from an equilibrium position in which no force is exerted on the piston by the member. The restoring force of the joining member is offset by the fluid pressure against the piston. The joining member may either be under tension or compression depending on where the member is anchored to the piston housing. As the fluid is removed from the first piston housing, the elastic or resilient member acts like a spring and pulls or pushes the piston back to an equilibrium position in which no forces are exerted on it by the joining membrane.

In those embodiments in which the first portion of the piston housing is proximal to the second portion of the piston housing, the first portion of the piston housing may optionally extend to the proximal end of the device. In such case, a separate inflation lumen may not be necessary as the inflation fluid may be supplied directly through the manifold to the first portion of the piston housing and/or may be directly removed from the first portion of the piston housing.

The connector element may be a wire or a rod made of a suitable metal such as stainless steel or a polymeric material. Where the device is to be operated in push mode, the connector element should be relatively incompressible and buckle resistance under a compressive force. Where the device is to be operated in pull mode, the connecting member can be made of any suitable material having a tensile strength so that the connecting element does not deform or break under tension.

In a preferred embodiment of the invention, the inventive medical device delivery system further comprises an accordion-like collapsible sheath 160 between piston housing 124 and medical device mounting region 108, as shown in FIGS. 1–4. The proximal end of collapsible sheath 160 is attached, desirably adhesively bonded, to the distal end of piston housing 124. Of course, other configurations are possible as well. For example, the apparatus may further comprise an outer tube in which at least a portion of catheter shaft 104 and piston/piston housing 124 are carried. In such case, the proximal end of collapsible sheath 160 may be fixedly attached to the distal end of such an outer tube. The distal end of collapsible sheath 160 is, in turn, attached, desirably adhesively bonded, to pull collar 164. Additional information about the collapsible sheath made be found in U.S. Pat. No. 5,534,007 to St. Germain and Olson, incorporated herein in its entirety by reference.

The inventive medical device may be constructed such that the retractable sheath is withdrawn into an outer catheter as described in commonly assigned patent U.S. Pat. No. 5,772,669 and commonly assigned and copending U.S. application Ser. No. 09/071,484 both of which are hereby incorporated in their entirety by reference. The pull back means disclosed therein may be modified using the piston system as disclosed herein.

Pull collar 164 is a ring-shaped member of stainless steel or preferably of a radio-opaque material such as gold affixed to the distal end of collapsible sheath 160 by an appropriate adhesive such as a urethane. Pull collar 164 is also attached, desirably adhesively bonded, to retractable sheath 112 either directly (as shown in FIGS. 1–3) or indirectly via a distal outer tube 168 as shown in FIG. 4.

Optional distal outer tube may be made of suitable materials, such as polymeric materials, as are known in the art.

The medical device delivery apparatus disclosed herein, when configured for use with a stent, may further comprise one or more bumpers 172 as are known in the art.

Additionally, radio-opaque markers may be included in the apparatus to facilitate positioning the medical device in the body.

Optionally, the medical device delivery apparatus may further comprise a balloon. Desirably, the balloon will be mounted about the medical device receiving region of the catheter. Where stents and grafts are to be delivered, the balloon may be used to expand, assist in expansion or seat the stent or graft. Where a balloon is included, the apparatus must be further modified to have a balloon inflation lumen capable of fluid communication with the balloon. Further, a manifold which can accommodate the balloon inflation lumen must be used.

The inventive apparatuses may further comprise other standard components as are known to be used with catheters, including a manifold, as discussed above. Any suitable manifold which is capable of delivering a fluid to an inflation lumen may be used.

Generally, connections between the various polymer components may be made utilizing suitable medical grade adhesives or thermal bonds well known in the art. Connections between metallic components may be made, for example, by utilizing a solder, braze or weld.

The inventive medical device delivery apparatus may further comprise an outer stiffening shaft such as that disclosed in commonly assigned patents, U.S. Pat. No. 5,571,168 to Del Toro and U.S. Pat. No. 5,733,267 to Del Toro, both of which are incorporated herein in their entirety by reference.

The inventive medical device delivery apparatus, in all of its embodiments, may be used to deliver medical devices such as stents, vena cava filters and grafts. Other suitable medical devices may also be delivered.

The present invention is also directed to methods of delivering a medical device to a desired bodily location using the inventive apparatuses disclosed herein. More particularly, the method involves providing an inventive medical device delivery apparatus as disclosed above with a medical device received about the medical device receiving region. At least a portion of the apparatus is inserted in a bodily vessel distal end first. The distal of the apparatus and hence, the medical device, is advanced to a desired location. A fluid is then supplied under pressure to the first piston housing so as to actuate the piston and retract the sheath. The medical device is then deployed and the medical device delivery apparatus withdrawn from the bodily vessel. Desirably, the medical device delivered to the bodily location will be a stent, graft or vena cava filter. More desirably, the device will be a self-expanding, balloon expandable or balloon assisted expandable stent. Optionally, the retractable sheath may be closed again by removing the inflation fluid from the first piston housing and pulling a vacuum on the first piston housing or by a restorative spring-like force of a member connecting the piston to the piston housing. The apparatus may then be removed from the body.

In another embodiment, the apparatus is inserted as above. However, the first piston housing of the apparatus has a fluid therein. The piston is then actuated by removing the fluid therefrom and applying a vacuum to the piston housing. Alternatively, where the piston is attached to the piston housing by an elastic, resilient or otherwise spring-like member, the piston is initially displaced from its equilibrium position by the fluid present in the first piston housing. Upon removal of the fluid from the first piston housing, the piston will return to its equilibrium position via a spring-like restoration force exerted by the member. In either case, the movement of the piston causes retraction of the sheath, allowing for deployment of the medical device such as a stent. Optionally, the sheath may be closed following deployment of the medical device by adding fluid back to the first piston housing. The apparatus may then be removed from the body.

Where the apparatus comprises a balloon, the inventive methods may further comprise the step of inflating the balloon so as to dilate a lesion, expand, assist in expanding or seat a medical device such as a stent.

For the purposes of this disclosure, the terms medical device receiving region and medical device mounting region as used herein are intended to describe a region of the catheter on which or about which a medical device is mounted. The device may be in physical contact with the region, as in the case of a stent crimped to the catheter. Alternatively, the medical device may surround at least a portion of the region, as in the case of certain self-expanding stents that are held in place by a sheath although they do not actually contact the catheter.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A medical device delivery apparatus for delivery of a medical device to a desired bodily location, the apparatus having a proximal and a distal end and comprising:
   an elongate flexible catheter having proximal and distal ends, the catheter having a medical device receiving region at the distal end thereof;
   a retractable sheath for surrounding the medical device receiving region of the elongate catheter;
   a retraction device for retracting the retractable sheath, the retraction device comprising:
     a piston housing having a first portion and a second portion therein, the first and second portions separated by a movable piston contained within the housing,
     the first portion having an inflatable element therein, and
     a connecting member, one end of which is in mechanical communication with the retractable sheath, the other end of the connecting member connected to the piston.

2. The medical device delivery apparatus of claim 1 further comprising a medical device surrounding the medical device receiving region of the flexible catheter.

3. The medical device delivery apparatus of claim 2 wherein the medical device is selected from the group consisting of stents, vena cava filters and grafts.

4. The medical device delivery apparatus of claim 3 wherein the first portion of the piston housing extends to the proximal end of the device.

5. The medical device delivery apparatus of claim 3 further comprising an inflation lumen capable of fluid communication with the inflatable element.

6. The medical device delivery apparatus of claim 3 wherein the first portion of the piston housing is proximal of the second portion of the piston housing.

7. The medical device delivery apparatus of claim 6 wherein the connecting member is relatively rigid.

8. The medical device delivery apparatus of claim 3 wherein the first portion of the piston housing is distal of the second portion of the piston housing.

9. The medical device delivery apparatus of claim 3 wherein the connecting member is a wire.

10. The medical device delivery apparatus of claim 3 wherein the second portion of the piston housing is sealed.

11. The medical device delivery apparatus of claim 3 wherein the second portion of the piston housing has pressure relief openings therein.

12. The medical device delivery apparatus of claim 3 wherein the second portion of the piston housing has a bio-compatible fluid therein.

13. The medical device delivery apparatus of claim 3 wherein the inflatable element is accordion shaped.

14. The medical device delivery apparatus of claim 3 wherein the apparatus is configured in a configuration selected from the group consisting of a rapid exchange configuration, an over-the-wire configuration and a fixed-wire configuration.

15. The medical device delivery apparatus of claim 3 wherein the piston housing surrounds and is coaxial with a portion of the elongate flexible catheter.

16. The medical device delivery apparatus of claim 3 wherein a transverse cross-section of the piston housing extends across a substantial portion of a transverse cross-section of the apparatus in the region of the piston.

17. The medical device delivery apparatus of claim 1 wherein the piston is actuated by supplying a fluid to the inflatable element.

18. The medical device delivery apparatus of claim 1 wherein the inflatable element contains an inflation fluid therein and the piston is actuated is by removing at least some of the fluid from the inflatable element.

19. A medical device delivery apparatus for implantation of a medical device in a vessel comprising:
   an elongate flexible catheter having proximal and distal ends, the catheter having a medical device receiving region at the distal end thereof
   a retractable sheath surrounding at least a portion of the medical device receiving region;
   a retraction device for retracting the retractable sheath, the retraction device comprising:
     a piston housing having a first and a second portion therein, the first and second portions separated by a movable piston contained within the housing, the piston housing surrounding and coaxial with a portion of the elongate flexible catheter, and
     a connecting member, one end of which is in mechanical communication with the retractable sheath, the other end of the connecting member connected to the piston.

20. The medical device delivery apparatus of claim 19 further comprising a medical device surrounding the medical device receiving region of the flexible catheter near its distal end.

21. The medical device delivery apparatus of claim 20 wherein the medical device is selected from the group consisting of stents, vena cava filters and grafts.

22. The medical device delivery apparatus of claim 21 wherein the apparatus is configured in a configuration selected from the group consisting of a rapid exchange configuration, an over-the-wire configuration and a fixed-wire configuration.

23. The medical device delivery apparatus of claim 21 further comprising an inflation lumen capable of fluid communication with the first portion of the piston housing.

24. The medical device delivery apparatus of claim 23 further comprising an inflatable element within the first portion of the piston housing, the inflatable element capable of fluid communication with the inflation lumen.

25. The medical device delivery apparatus of claim 21 wherein the first portion of the piston housing is proximal of the second portion of the piston housing.

26. The medical device delivery apparatus of claim 25 wherein the first portion extends to the proximal end of the device.

27. The medical device delivery apparatus of claim 21 wherein the connecting member is relatively rigid.

28. The medical device delivery apparatus of claim 21 wherein the first portion of the piston housing is distal of the second portion of the piston housing.

29. The medical device delivery apparatus of claim 21 wherein the connecting member is a wire.

30. The medical device delivery apparatus of claim 21 wherein the second portion of the piston housing is sealed.

31. The medical device delivery apparatus of claim 21 wherein the second portion of the piston housing has pressure relief openings therein.

32. The medical device delivery apparatus of claim 21 wherein the second portion of the piston housing has a bio-compatible fluid therein.

33. The medical device delivery apparatus of claim 21 wherein the piston is slidably sealed to the catheter.

34. The medical device delivery apparatus of claim 19 wherein the piston is actuated by supplying a fluid to the first portion of the housing.

35. The medical device delivery apparatus of claim 19 wherein the first portion of the housing contains an inflation fluid therein and the piston is actuated is actuated by removing at least some of the fluid from the first portion of the housing.

36. A method for delivering a stent to a desired bodily location using the apparatus of claim 3 comprising the steps of:

providing a medical device delivery apparatus as in claim 3 wherein the medical device is a stent;

inserting at least a portion of the device in a bodily vessel;

advancing the stent to a desired location;

providing a source of fluid;

supplying the fluid under pressure to the inflatable element so as to actuate the piston and retract the sheath;

deploying the stent;

withdrawing the medical device delivery apparatus from the bodily vessel.

37. The method of claim 36 further comprising the step of priming the second portion of the piston housing.

38. A method for delivering a stent to a desired bodily location using the apparatus of claim 18 comprising the steps of:

providing a medical device delivery apparatus as in claim 18, the device further having a stent surrounding the medical device receiving region;

inserting at least a portion of the device in a bodily vessel;

advancing the stent to a desired location;

removing at least a portion of the fluid from the inflatable element so as to actuate the piston and retract the sheath;

deploying the stent;

withdrawing the medical device delivery apparatus from the bodily vessel.

39. A method for delivering a stent to a desired bodily location using the apparatus of claim 19 comprising the steps of:

providing a medical device delivery apparatus as in claim 19, the device further having a stent surrounding the medical device receiving region;

inserting at least a portion of the device in a bodily vessel;

advancing the stent to a desired location;

providing a source of fluid;

supplying the fluid under pressure to the inflatable element so as to actuate the piston and retract the sheath;

deploying the stent;

withdrawing the medical device delivery apparatus from the bodily vessel.

40. A method for delivering a stent to a desired bodily location using the apparatus of claim 35 comprising the steps of:

providing a medical device delivery apparatus as in claim 35, the device further having a stent surrounding the medical device receiving region;

inserting at least a portion of the device in a bodily vessel;

advancing the stent to a desired location;

providing a source of fluid;

removing at least a portion of the fluid from the inflatable element so as to actuate the piston and retract the sheath;

deploying the stent;

withdrawing the medical device delivery apparatus from the bodily vessel.

41. A method for delivering a medical device to a desired bodily location comprising the steps of:

providing a medical device delivery apparatus comprising:
  a) an elongate flexible catheter having proximal and distal ends, a medical device receiving region at the distal end thereof, a medical device mounted on the medical device receiving region;
  b) a retractable sheath for surrounding the medical device receiving region of the elongate catheter;
  c) a retraction device for retracting the retractable sheath, the retraction device comprising:
    i) a piston housing having a first portion and a second portion therein, the first and second portions separated by a movable piston contained within the housing, the first portion having a fluid therein; and
    ii) a connecting member, one end of which is in mechanical communication with the retractable sheath, the other end of the connecting member connected to the piston;

inserting at least a portion of the apparatus in a bodily vessel;

advancing the medical device to a desired location;

removing at least a portion of the fluid from the first portion of the piston housing so as to actuate the piston and retract the sheath;

deploying the medical device;

withdrawing the medical device delivery apparatus from the bodily vessel.

* * * * *